United States Patent
Yoo et al.

(10) Patent No.: US 9,902,679 B2
(45) Date of Patent: Feb. 27, 2018

(54) RECOVERY METHOD AND RECOVERY DEVICE FOR (METH) ACRYLIC ACID

(71) Applicant: LG CHEM, LTD., Seoul (KR)

(72) Inventors: Sul Hee Yoo, Daejeon (KR); Se Won Baek, Daejeon (KR); Jong Hun Song, Daejeon (KR); Yoon Jae Min, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/325,687

(22) PCT Filed: Jun. 24, 2015

(86) PCT No.: PCT/KR2015/006435
§ 371 (c)(1),
(2) Date: Jan. 11, 2017

(87) PCT Pub. No.: WO2016/043412
PCT Pub. Date: Mar. 24, 2016

(65) Prior Publication Data
US 2017/0158594 A1 Jun. 8, 2017

(30) Foreign Application Priority Data

Sep. 17, 2014 (KR) .................. 10-2014-0123876

(51) Int. Cl.
*C07C 51/42* (2006.01)
*C07C 51/46* (2006.01)
*B01D 3/36* (2006.01)

(52) U.S. Cl.
CPC .............. *C07C 51/46* (2013.01); *B01D 3/36* (2013.01)

(58) Field of Classification Search
CPC ........... C07C 51/46; C07C 51/44; B01D 3/36; C07B 63/00
See application file for complete search history.

(56) References Cited

U.S. PATENT DOCUMENTS

| | | |
|---|---|---|
| 4,166,774 A | 9/1979 | Wagner |
| 5,831,124 A | 11/1998 | Machhammer et al. |
| 6,433,222 B1 | 8/2002 | Eck et al. |
| 7,151,194 B2 | 12/2006 | Ueno et al. |
| 9,517,997 B2 | 12/2016 | Baek et al. |
| 2009/0253934 A1 | 10/2009 | Ho et al. |
| 2010/0273970 A1 | 10/2010 | Koestner et al. |
| 2013/0118892 A1* | 5/2013 | Meier .................... B01D 3/141 203/53 |

FOREIGN PATENT DOCUMENTS

| | | |
|---|---|---|
| JP | 2003-321419 A | 11/2003 |
| JP | 2004-358387 | * 12/2004 |
| JP | 2004-358387 A | 12/2004 |
| JP | 4520637 B2 | 8/2010 |
| JP | 2013-107894 A | 6/2013 |
| JP | 5368673 B2 | 12/2013 |
| KR | 10-2004-0108609 A | 12/2004 |
| KR | 10-0514026 B1 | 12/2005 |
| KR | 10-2010-0107029 A | 10/2010 |
| KR | 10-2014-0018791 A | 2/2014 |

OTHER PUBLICATIONS

JP2004-358387 translated 25 pages, 2004.*
JP2004-358387 p. 1-25 (Year: 2004).*

* cited by examiner

*Primary Examiner* — Yevgeny Valenrod
*Assistant Examiner* — Blaine G Doletski
(74) *Attorney, Agent, or Firm* — Dentons US LLP

(57) ABSTRACT

Provided are a method and an apparatus for recovering (meth)acrylic acid. The recovering method is used to save the energy required for a process of recovering (meth)acrylic acid because a process of separating high-boiling point by-products can be omitted, and to minimize a possibility of (meth)acrylic acid polymerization during the process of recovering (meth)acrylic acid. Therefore, the recovering method is used to obtain (meth)acrylic acid with less energy in a high yield.

7 Claims, 2 Drawing Sheets

[FIG. 1]
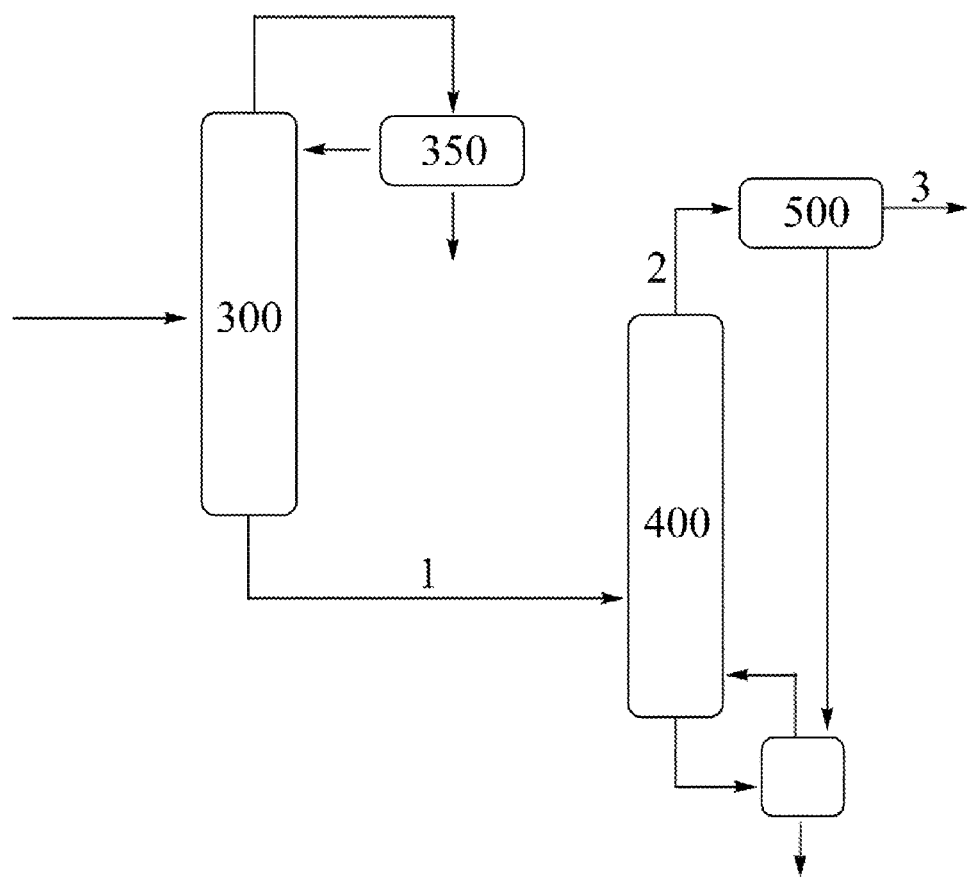

[FIG. 2]
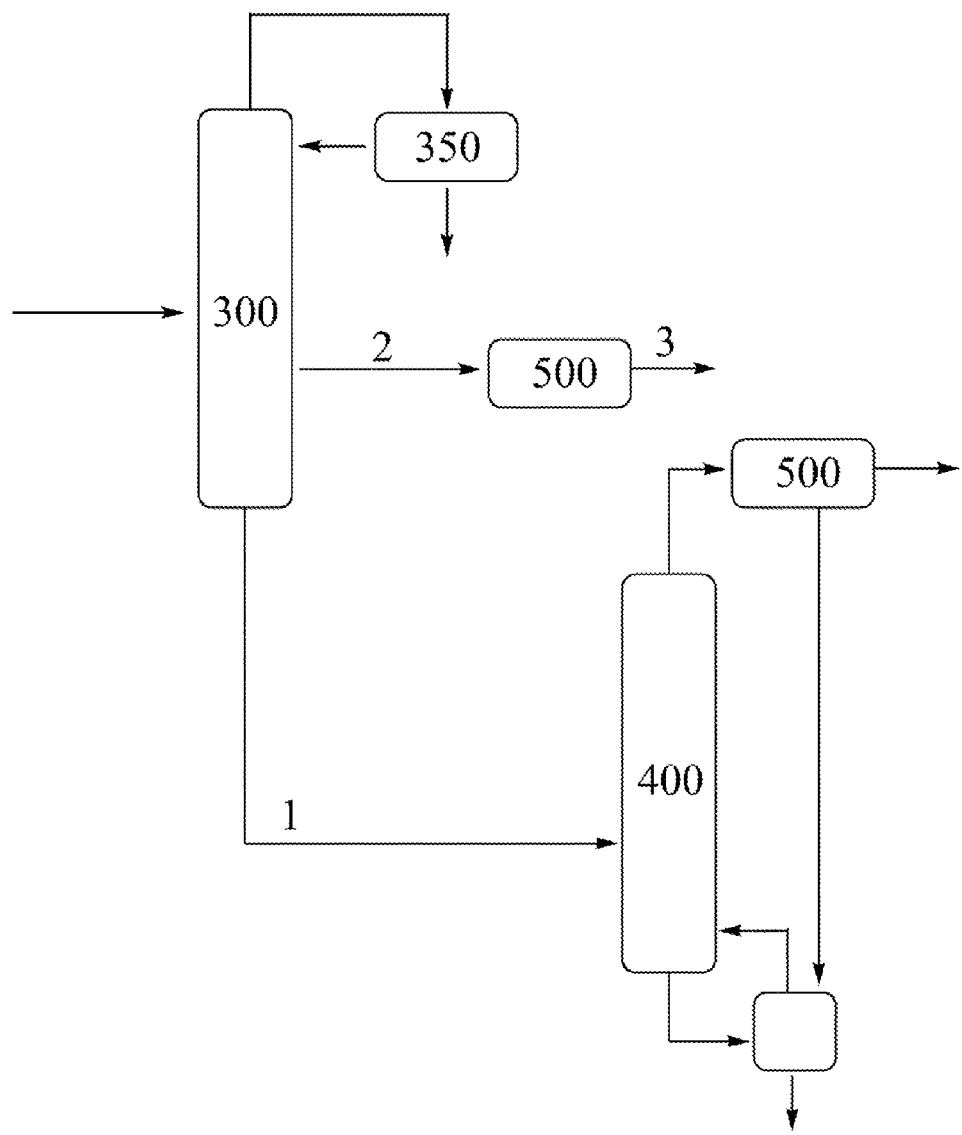

RECOVERY METHOD AND RECOVERY DEVICE FOR (METH) ACRYLIC ACID

CROSS REFERENCE TO RELATED APPLICATION

This application is a National Stage Application of International Application No. PCT/KR2015/006435 filed on Jun. 24, 2015, which claims the benefit of Korean Patent Application No. 10-2014-0123876 filed on Sep. 17, 2014, all of which are hereby incorporated by reference in their entirety for all purposes as if fully set forth herein.

TECHNICAL FIELD

The present invention relates to a method for efficiently recovering (meth)acrylic acid and an apparatus therefor.

BACKGROUND ART

Generally, (meth)acrylic acid is prepared by gas-phase oxidation of propane, propylene, (meth)acrolein, etc. in the presence of a catalyst. For example, propane and propylene are converted to (meth)acrylic acid via (meth)acrolein by gas-phase oxidation in the presence of an appropriate catalyst in a reactor, and a reaction product gas mixture including (meth)acrylic acid, non-reacted propane or propylene, (meth)acrolein, inert gas, carbon dioxide, water vapor, and various organic by-products (acetic acid, low-boiling point by-products, high-boiling point by-products, etc.) is obtained in the back end of the reactor.

The (meth)acrylic acid-containing gas mixture contacts an absorption solvent containing water in a (meth)acrylic acid absorption tower, and obtained as a (meth)acrylic acid aqueous solution. Non-soluble gas from which (meth)acrylic acid is discharged is recycled to the synthetic reaction of (meth)acrylic acid, or a part thereof is converted to harmless gas by incineration, and discharged. The (meth)acrylic acid aqueous solution is obtained as (meth)acrylic acid by extraction, distillation, and purification.

Meanwhile, various methods have been suggested to improve recovery efficiency of (meth)acrylic acid by controlling process conditions or process order. A known representative method is a method for separating water and acetic acid from the (meth)acrylic acid aqueous solution obtained in the (meth)acrylic acid absorption tower by azeotropic distillation using a hydrophobic solvent in a distillation column.

In detail, by the azeotropic distillation method, water and acetic acid are recovered from the top portion of the distillation column and (meth)acrylic acid is recovered from the bottom portion of the distillation column. However, (meth) acrylic acid recovered from the bottom portion of the distillation column is recovered as a mixture with high-boiling point by-products, etc., and therefore, the liquid discharged from the bottom portion of the distillation column must be further distilled in order to remove high-boiling point by-products. A high-boiling point by-product separation process of removing high-boiling point by-products from the bottom discharge liquid requires a large amount of energy and also generates a problem that (meth) acrylic acid is exposed to high temperature during the process.

DISCLOSURE

Technical Problem

The present invention provides a method for recovering (meth)acrylic acid with less energy in a high yield, and an apparatus therefor.

Technical Solution

The present invention provide a method for recovering (meth)acrylic acid, including a distillation process of distilling a feed containing 10 to 90% by weight of (meth) acrylic acid, 10 to 90% by weight of a solvent, and a residual amount of impurity to obtain crude (meth)acrylic acid containing 80% by weight or more of (meth)acrylic acid, 5% by weight or less of the solvent, and 3% by weight or less of (meth)acrylic acid dimer from the side portion of a distillation tower.

For example, the recovering method may further include an absorption process of obtaining a (meth)acrylic acid solution by contacting a (meth)acrylic acid-containing gas mixture with an absorption solvent. Further, the recovering method may further include an extraction process of obtaining a (meth)acrylic acid extract solution and a raffinate solution by contacting the (meth)acrylic acid solution with an extraction solvent.

The crude (meth)acrylic acid may be discharged from a section placed 50% to 100% from the top section of the distillation tower.

A liquid-phase or gas-phase crude (meth)acrylic acid may be obtained from the side portion of the distillation tower. Further, (meth)acrylic acid corresponding to 30 to 90% by weight of the total (meth)acrylic acid contained in the feed may be recovered from the side portion of the distillation tower.

The recovering method may further include a high-boiling point by-product separation process of obtaining crude (meth)acrylic acid from the top portion of high-boiling point by-product separation tower by distilling a bottom discharge liquid discharged from the bottom portion of the distillation tower. Further, the recovering method may further include a crystallization process of recrystallizing the obtained crude (meth)acrylic acid.

Meanwhile, the present invention provides an apparatus for recovering (meth)acrylic acid including the distillation tower and a crystallizer. In detail, the recovering apparatus may include the distillation tower equipped with a feed inlet, and top, side, and bottom outlets; and the crystallizer equipped with a crude (meth)acrylic acid inlet connected to the side outlet of the distillation tower via a crude (meth) acrylic acid transfer line, and a (meth)acrylic acid outlet from which (meth)acrylic acid obtained by recrystallization of the introduced crude (meth)acrylic acid is discharged.

The recovering apparatus may further include a (meth) acrylic acid absorption tower which is equipped with a gas mixture inlet to which a (meth)acrylic acid-containing gas mixture is supplied, and an aqueous solution outlet from which the (meth)acrylic acid solution obtained by contacting the gas mixture with the absorption solvent is discharged. Further, the recovering apparatus may further include a (meth)acrylic acid extraction tower which is equipped with an aqueous solution inlet connected to the aqueous solution outlet of the absorption tower via an aqueous solution transfer line, an extract outlet from which a (meth)acrylic acid extract solution obtained by contacting the introduced (meth)acrylic acid solution with an extraction solvent is discharged, and a raffinate outlet in which a raffinate thereof is left, and then from which the raffinate thereof is discharged.

Effect of the Invention

A method for recovering (meth)acrylic acid according to an embodiment is used to save the energy required for a process of recovering (meth)acrylic acid because a process of separating high-boiling point by-products can be omitted, and to minimize a possibility of (meth)acrylic acid polymerization during the process of recovering (meth)acrylic acid. Therefore, the recovering method is used to obtain (meth)acrylic acid with less energy in a high yield.

DESCRIPTION OF DRAWINGS

FIG. 1 is a view illustrating a general apparatus for recovering (meth)acrylic acid; and
FIG. 2 is a view illustrating an apparatus for recovering (meth)acrylic acid according to an exemplary embodiment.

REFERENCE NUMERAL

300: Distillation tower
350: Phase separator
400: High-boiling point by-product separation tower
500: Crystallizer

DETAILED DESCRIPTION OF THE EMBODIMENTS

Hereinafter, a method and an apparatus for recovering (meth)acrylic acid according to specific embodiments of the present invention will be described.

An embodiment of the present invention provides a method for recovering (meth)acrylic acid, including a distillation process of distilling a feed containing 10 to 90% by weight of (meth)acrylic acid, 10 to 90% by weight of a solvent, and a residual amount of impurity to obtain crude (meth)acrylic acid containing 80% by weight or more of (meth)acrylic acid, 5% by weight or less of the solvent, and 3% by weight or less of (meth)acrylic acid dimer from the side portion of a distillation tower.

In the conventional method for recovering (meth)acrylic acid, as shown in FIG. 1, a (meth)acrylic acid solution is introduced into a distillation tower 300, the (meth)acrylic acid solution introduced into the distillation tower 300 is distilled to recover water and acetic acid from the top portion of the distillation tower 300, and a discharge liquid (stream 1 of FIG. 1) containing (meth)acrylic acid from the bottom portion of the distillation tower 300. Thereafter, the liquid (stream 1 of FIG. 1) discharged from the bottom portion of the distillation tower 300 is introduced into a high-boiling point by-product separation tower 400, and high-boiling point by-products contained in the liquid discharged from the bottom portion are separated to recover crude (meth) acrylic acid from the top portion of the high-boiling point by-product separation tower 400. Further, the crude (meth) acrylic acid (stream 2 of FIG. 1) obtained from the top portion of the high-boiling point by-product separation tower 40 is recrystallized in a crystallizer 500 to obtain pure (meth)acrylic acid (stream 3 of FIG. 1). However, this conventional recovering method must include a process of separating high-boiling point by-products from the (meth) acrylic acid mixture, thereby requiring a lot of energy and generating a problem of low yield of (meth)acrylic acid due to increased production of Michael adducts such as dimers, trimers, and oligomers resulting from a reaction between (meth)acrylic acids during the process of separating high-boiling point by-products.

In order to solve this problem, a specific embodiment of the present invention employs a distillation process of obtaining crude (meth)acrylic acid from the side portion of the distillation tower 300, as shown in FIG. 2, as a distillation process of removing a solvent from the (meth)acrylic acid mixture dissolved in a solvent such as an absorption solvent or an extraction solvent. As this process is employed, a process of separating high-boiling point by-products that is generally required after the distillation process may be omitted, the production yield of (meth)acrylic acid may be increased, and a large amount of energy may be saved. If necessary, the process of separating the high-boiling point by-products may be employed, but the amount of the sample injected to the process of separating high-boiling point by-products and the size of the high-boiling point by-product separation tower may be greatly reduced, thereby remarkably reducing a load applied to the process of separating high-boiling point by-products.

The recovering method includes a distillation process of obtaining crude (meth)acrylic acid from the side portion of the distillation tower by distilling a feed containing (meth) acrylic acid and a solvent. As used herein, the term "(meth) acrylic acid" refers to acrylic acid, methacrylic acid, or a mixture thereof.

The feed may be a (meth)acrylic acid solution obtained by various methods known in the art to which the present invention pertains.

For example, the feed may be the (meth)acrylic acid solution which is obtained by contacting a (meth)acrylic acid-containing gas mixture obtained by a synthetic reaction of (meth)acrylic acid with an absorption solvent. Therefore, the recovering method may further include an absorption process of obtaining the feed by contacting the (meth)acrylic acid-containing gas mixture with the absorption solvent.

The (meth)acrylic acid-containing gas mixture may be obtained by, for example, gas-phase oxidation of one or more compounds (raw compounds) selected from the group consisting of propane, propylene, butane, isobutylene, and (meth)acrolein in the presence of a catalyst. The (meth) acrylic acid-containing gas mixture may include (meth) acrylic acid, a non-reacted raw compound, (meth)acrolein, inert gas, carbon monoxide, carbon dioxide, water vapor, and various organic by-products (acetic acid, low-boiling point by-products, high-boiling point by-products, etc.). Herein, the 'low-boiling point by-products (light ends)' or 'high-boiling point by-products (heavies)' are a kind of by-products that may be generated during preparation and recovery of the desired (meth)acrylic acid, and collectively refer to compounds having a molecular weight lower or higher than that of (meth)acrylic acid.

The (meth)acrylic acid solution may be provided by contacting the (meth)acrylic acid-containing gas mixture with the absorption solvent. Non-limiting example thereof may be a (meth)acrylic acid solution that is obtained by introducing the (meth)acrylic acid-containing gas mixture into the (meth)acrylic acid absorption tower and contacting the gas mixture with the absorption solvent.

As the (meth)acrylic acid absorption tower, a packed tower or a multistage tray tower may be used in order to improve contact efficiency of the (meth)acrylic acid-containing gas mixture and the absorption solvent. Herein, the interior of the packed tower may be packed with a filler such as raschig ring, pall ring, saddle, gauze, or structured packing.

The (meth)acrylic acid-containing gas mixture may be introduced into the bottom portion of the absorption tower, and the absorption solvent may be introduced into the top portion of the absorption tower, thereby increasing absorption efficiency of the gas mixture. The absorption solvent may include water such as tap water, distilled water, or deionized water. Further, the absorption solvent may include recycling process water introduced from other process (e.g., water recycled from the top of the distillation tower). Therefore, the absorption solvent may include a trace amount of organic by-products, for example, acetic acid, etc., which are introduced from other process. However, considering the absorption efficiency of (meth)acrylic acid, the content of the organic by-products in the absorption solvent which is introduced into the absorption tower may be controlled below 15% by weight.

The (meth)acrylic acid absorption tower may be operated at an internal pressure of 1 to 1.5 bar or 1 to 1.3 bar and an internal temperature of 50 to 100° C. or 50 to 80° C., considering the condensation conditions of (meth)acrylic acid and moisture content conditions according to saturated water vapor pressure. As a result, the (meth)acrylic acid solution may be discharged to the bottom portion of the (meth)acrylic acid absorption tower, and (meth)acrylic acid-stripped non-condensable gas may be discharged to the top portion of the absorption tower.

The absorption process may be performed by various methods such as a method of injecting the (meth)acrylic acid-containing gas mixture into a container containing the absorption solvent, in addition to the method of using the (meth)acrylic acid absorption tower.

If the absorption process is employed in the recovering method, the (meth)acrylic acid solution obtained from the absorption process may be introduced as a feed into the distillation tower 300, as shown in FIG. 2. For example, the (meth)acrylic acid solution obtained from the bottom portion of the (meth)acrylic acid absorption tower may be introduced into the distillation tower via a transfer line which connects the (meth)acrylic acid absorption tower and the distillation tower.

Meanwhile, in the absorption process, water is mainly used as the absorption solvent for absorbing (meth)acrylic acid from the (meth)acrylic acid-containing gas mixture. Therefore, in order to improve efficiency of a subsequent distillation process, the recovering method may further include an extraction process of obtaining a (meth)acrylic acid extract solution and a raffinate solution by contacting the (meth)acrylic acid solution with the extraction solvent.

The extraction process may be performed to remove most water contained in the (meth)acrylic acid solution by supplying the (meth)acrylic acid solution to the extraction tower.

In detail, the (meth)acrylic acid solution supplied to the extraction tower contacts the extraction solvent in the extraction tower, and is discharged as an extract solution in which a considerable amount of (meth)acrylic acid is dissolved, and a raffinate solution deprived of the considerable amount of (meth)acrylic acid. In this regard, the relatively light extract solution may be obtained from the top outlet of the extraction tower, and the relatively heavy raffinate solution may be obtained from the bottom outlet of the extraction tower.

As the extraction solvent, a solvent having solubility for (meth)acrylic acid and hydrophobicity may be used. Considering the kind and physical properties of the solvent used in the subsequent distillation process, the extraction solvent may be a solvent having a lower boiling point than (meth)acrylic acid. For example, the extraction solvent may be a hydrophobic solvent having a boiling point of 120° C. or lower, 10° C. to 120° C., or 50° C. to 120° C. Specifically, the extraction solvent may be one or more solvents selected from the group consisting of benzene, toluene, xylene, n-heptane, cycloheptane, cycloheptene, 1-heptene, ethyl benzene, methylcyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

By contacting the (meth)acrylic acid solution with the extraction solvent in the extraction tower, most water contained in the (meth)acrylic acid solution may be removed. Through this extraction process, the (meth)acrylic acid extract solution has a low water content. Therefore, when it is introduced as a feed into the distillation tower 300, a load applied to the distillation process is reduced, thereby improving energy efficiency of the whole process. Further, the load applied to the distillation process is reduced to minimize (meth)acrylic acid polymerization which may occur during distillation, thereby obtaining more improved recovery efficiency of (meth)acrylic acid.

Further, the feed may include both the (meth)acrylic acid solution obtained from the absorption process and the (meth) acrylic acid extract solution obtained from the extraction process. For example, at least a part of the (meth)acrylic acid solution obtained from the above described absorption process may be introduced into the distillation process via the extraction process, and the rest may be directly introduced into the distillation process.

The distillation process is a process of distilling a solvent such as the absorption solvent and the extraction solvent by distilling a solution which is obtained by contacting the (meth)acrylic acid-containing gas mixture produced by a synthetic reaction of (meth)acrylic acid with an absorption solvent, or a solution which is obtained by replacing the absorption solvent of the solution with an extraction solvent susceptible to distillation for efficiency of the distillation process. Therefore, the distillation process may be performed to distill the feed containing a large amount of solvents, thereby providing crude (meth)acrylic acid, from which most solvents are removed. Specifically, the feed may be provided by the absorption process or the extraction process, and may include 10 to 90% by weight, 20 to 80% by weight, or 20 to 70% by weight of the solvent, based on the total components.

Further, for efficient distillation of the feed, the feed may include 10% by weight or more of (meth)acrylic acid, based on the total components. Specifically, the feed may include 10 to 90% by weight, 50 to 90% by weight, or 50 to 80% by weight of (meth)acrylic acid, based on the total components. The feed may include a non-reacted raw compound, (meth) acrolein, various organic by-products such as low-boiling point by-products and high-boiling point by-products generated by the synthetic reaction of (meth)acrylic acid, and various impurities generated during the recovery process, in addition to (meth)acrylic acid and the solvent.

The distillation process may be performed to remove the solvent such as water and by-products from the feed, thereby discharging (crude)(meth)acrylic acid containing 80% by weight or more, 90% by weight or more, 95% by weight or more, or 99% by weight or more of (meth)acrylic acid and 5% by weight or less, 3% by weight or less, or 1% by weight or less of the solvent. In particular, the method for recovering (meth)acrylic acid according to an embodiment may be performed to discharge crude (meth)acrylic acid from not the bottom portion but the side portion of the distillation tower 300. Thus, crude (meth)acrylic acid containing 3% by weight or less, 1% by weight or less, or 0.5% by weight or less of (meth)acrylic acid dimer may be discharged. Accordingly, even though the process of separating high-boiling point by-products is omitted, highly pure (meth)acrylic acid may be provided. In this regard, it is preferable that the crude (meth)acrylic acid is composed of only (meth)acrylic acid by completely removing impurities such as solvents and (meth)acrylic acid dimers. Therefore, the upper limit of the (meth)acrylic acid may be 100% by weight, and the lower limit of the solvents and (meth)acrylic acid dimers may be 0% by weight. Further, the side portion of the distillation tower 300 means a portion excluding an overhead portion and a bottom portion.

As the distillation tower, a packed column packed with a filler or a multistage tray column may be used, and specifically, a sieve tray column or a dual flow tray column may be used.

The feed may be introduced into the center section of the distillation tower for efficient distillation. For example, the feed may be introduced to the section located 40 to 60% from the top section of the distillation tower.

In this regard, to efficiently separate (meth)acrylic acid included in the feed from the components such water, acetic acid, or the extraction solvent, the distillation may be performed by azeotropic distillation. As an azeotropic solvent applied to the azeotropic distillation, a hydrophobic azeotropic solvent that forms an azeotrope with water and acetic acid and not with (meth)acrylic acid may be used. As the hydrophobic azeotropic solvent, a solvent having a lower boiling point than (meth)acrylic acid may be used. Specifically, the hydrophobic azeotropic solvent may be one or more selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

The azeotropic solvent may be introduced into the top portion of the distillation tower. Therefore, the feed introduced to the distillation tower 300 may contact the azeotropic solvent introduced into the top portion of the distillation tower, and may be heated to a proper temperature, leading to distillation by evaporation and condensation. Specifically, heat may be introduced into the distillation tower via a reboiler at the bottom of the distillation tower. More specifically, for efficient distillation of the feed, the temperature of the overhead portion may be controlled below about 45° C. through the reboiler.

Further, for efficient distillation of the feed, the pressure of the overhead portion may be controlled to about 70 torr to 150 torr.

Through this distillation process, the components having a low boiling point in the feed may be discharged from the distillation tower 300, together with the azeotropic solvent. In this regard, the liquid discharged from the top portion of the distillation tower 300 may be introduced into a phase separator 350, and then recycled after a predetermined treatment. Herein, the phase separator 350 is an apparatus of separating immiscible liquids by gravitational forces or centrifugal forces. A relatively light liquid (e.g., an organic phase) may be recovered from the top portion of the phase separator 350 and a relatively heavy liquid (e.g., an aqueous phase) may be recovered from the bottom portion of the phase separator 350.

For example, the liquid discharged from the top portion of the distillation tower 300 may be separated into an organic phase containing the azeotropic solvent and an aqueous phase containing water in the phase separator 350. Herein, the separated organic phase may be introduced into the top portion of the distillation tower 300, and used as the azeotropic solvent.

Meanwhile, while the feed is passed through the (meth)acrylic acid absorption tower, the extraction tower, or the distillation tower 300, at least a part of the (meth)acrylic acid included in the feed may form dimers or oligomers. To minimize the polymerization of (meth)acrylic acid, a general polymerization inhibitor may be added to the distillation tower 300.

In the conventional recovering method, (meth)acrylic acid is discharged from the bottom portion of the distillation tower, and therefore, high-boiling point by-products such as (meth)acrylic acid polymers and the polymerization inhibitor in addition to (meth)acrylic acid may be included in the liquid discharged from the bottom portion of the distillation tower.

In the recovering method according to a specific embodiment of the present invention, however, crude (meth)acrylic acid is recovered from the side portion of the distillation tower, thereby obtaining crude (meth)acrylic acid having a very low content of the high-boiling point by-products and the polymerization inhibitor. Further, the crude (meth)acrylic acid obtained from the side portion of the distillation tower has high purity, and thus it is near colorless. Consequently, a high-purity product may be obtained through a crystallization process.

In detail, the crude (meth)acrylic acid may be discharged from a section placed lower than the section into which the feed of the distillation tower is introduced. The section in the distillation tower means a discharge tube placed on the tray, and the uppermost portion of the distillation tower differs from the overhead section in the terms of position, and the lowermost portion of the distillation tower differs from the bottom section in the terms of position. More specifically, the crude (meth)acrylic acid may be discharged from the section placed 50% to 100% from the top section of the distillation tower. If a distillation tower having total 30 sections is used, the crude (meth)acrylic acid may be discharged from any one section of the $15^{th}$ section to the $30^{th}$ section of the distillation tower.

The crude (meth)acrylic acid may be recovered in a liquid-phase or gas-phase from the side portion of the distillation tower. The phase of the crude (meth)acrylic acid obtained from the side portion of the distillation tower may vary depending on the insertion point of the side discharge tube. In detail, the side discharge tube is inserted into the location where a liquid on the tray of the section discharging crude (meth)acrylic acid is collected, thereby forcibly discharging the liquid-phase crude (meth)acrylic acid to the side portion of the tower. Alternatively, the side discharge tube is inserted into the location where a gas, not a liquid, on the tray of the section discharging crude (meth)acrylic acid is collected, thereby discharging the gas-phase crude (meth)acrylic acid to the side portion of the tower through a condensation process in a condenser. In this regard, to efficiently recover the gas-phase crude (meth)acrylic acid from the side portion of the tower, the condenser may be maintained at a lower pressure than the operating pressure of the distillation tower.

Referring to the after-mentioned Experimental Example 1, if the crude (meth)acrylic acid discharged from the side portion of the distillation tower is in a gas-phase, it has a low content of high-boiling point by-products such as (meth) acrylic acid dimers, compared to the liquid phase. Referring to the after-mentioned Experimental Example 2, although the process of distilling high-boiling point by-products is omitted, the gas-phase crude (meth)acrylic acid provides (meth)acrylic acid having high purity equivalent to that of the (meth)acrylic acid which is recovered through the process of distilling high-boiling point by-products. Therefore, it is preferable that the gas-phase crude (meth)acrylic acid is recovered from the side portion of the distillation tower, in terms of providing high-purity (meth)acrylic acid.

The amount of (meth)acrylic acid corresponding to 30 to 90% by weight of the total (meth)acrylic acid included in the feed may be recovered from the side portion of the distillation tower. If the amount of (meth)acrylic acid recovered from the side portion of the distillation tower is less than 30% by weight of the total (meth)acrylic acid included in the feed, the residual amount of (meth)acrylic acid may be recovered from the bottom portion of the distillation tower. Since the liquid discharged from the bottom of the distillation tower includes high-boiling point by-products and a polymerization inhibitor, a process of separating high-boiling point by-products is required in order to provide crude (meth)acrylic acid having a purity high enough to be introduced into the crystallization process. Therefore, in the case where the amount of (meth)acrylic acid recovered from the side portion of the distillation tower is less than 30% by weight, a large amount of the liquid discharged from the bottom portion is introduced to the distillation process of high-boiling point by-products, leading to energy loss. In contrast, in the case where the amount of (meth)acrylic acid recovered from the side portion of the distillation tower is more than 90% by weight of the total (meth)acrylic acid included in the feed, high-boiling point components are accumulated at the bottom of the tower to increase viscosity of the liquid at the bottom of the tower or to clog the tube in the apparatus, thereby making it impossible to continue the operation of the distillation tower. Therefore, (meth) acrylic acid is recovered in an amount within the above range from the side portion of the distillation tower, and then introduced into the crystallization process, thereby obtaining high-purity (meth)acrylic acid and saving a large amount of energy by reducing the amount of the liquid discharged from the bottom portion.

In order to optimize the above effects, the amount of (meth)acrylic acid corresponding to about 40 to 90% by weight or about 40 to 85% by weight of the total (meth) acrylic acid included in the feed may be recovered from the side portion of the distillation tower.

The amount of (meth)acrylic acid obtained from the side portion of the distillation tower may be controlled by controlling a flow rate of a discharge pump or a pressure of the condenser placed with the side discharge tube.

The (meth)acrylic acid, high-boiling point by-products such as (meth)acrylic acid polymers, and polymerization inhibitor may be discharged to the bottom portion of the distillation tower 300. Therefore, in order to further recover (meth)acrylic acid from the liquid discharged from the bottom portion, the recovering method may further include a high-boiling point by-product-separating process of obtaining crude (meth)acrylic acid from the top portion of the high-boiling point by-product separation tower by distilling the liquid discharged from the bottom portion of the distillation tower.

In detail, as shown in FIG. 2, the liquid discharged from the bottom portion of the distillation tower is introduced into the high-boiling point by-product separation tower 400, thereby separating high-boiling point by-products included in the liquid discharged from the bottom portion. Further, crude (meth)acrylic acid may be further obtained from the top portion of the high-boiling point by-product separation tower 400. In this regard, the high-boiling point by-product-separating process may be performed under general conditions, and thus the process conditions are not particularly limited.

The crude (meth)acrylic acid recovered through the process may be subjected to an additional crystallization process, thereby obtaining (meth)acrylic acid with a higher purity.

In detail, as shown in FIG. 2, crude (meth)acrylic acid (stream 2 of FIG. 2) obtained from the side portion of the distillation tower 300 may be directly introduced into a crystallizer 500 without passing through the high-boiling point by-product separation tower 400. However, the liquid (stream 1 of FIG. 2) discharged from the bottom portion of the distillation tower 300 may be introduced into the crystallizer 500 via the high-boiling point by-product separation tower 400, because the liquid contains a large amount of high-boiling point by-products. If the liquid discharged from the bottom portion of the distillation tower 300 contains a small amount of (meth)acrylic acid, it may be directly introduced into an acrylic acid dimer-decomposing process without passing through the high-boiling point by-product separation tower 400. As shown in FIG. 2, therefore, if crude (meth)acrylic acid is recovered from the side portion of the distillation tower 300, the liquid may be directly introduced into the (meth)acrylic acid dimer-decomposing process without passing through the process of separating high-boiling point by-products, thereby recovering (meth)acrylic acid from the bottom section liquid.

The crude (meth)acrylic acid introduced into the crystallizer may be recrystallized to provide high-purity (meth) acrylic acid. A crystallization process of the crude (meth) acrylic acid may be performed under general conditions. For non-limiting examples, dynamic crystallization of the crude (meth)acrylic acid may be performed to provide high-purity (meth)acrylic acid. In detail, to perform dynamic crystallization of the crude (meth)acrylic acid, liquid-phase crude (meth)acrylic acid may be allowed to flow in the form of a falling film in the inner wall of the tube. A temperature of the tube is controlled to be below a freezing point of (meth) acrylic acid and induce deposition of crystals on the inner wall of the tube. Subsequently, the temperature of the tube is increased near a freezing point of (meth)acrylic acid to sweat about 5% by weight of (meth)acrylic acid. The sweated residual liquid was pumped out of the tube, and crystals formed on the inner wall of the tube were recovered to obtain high-purity (meth)acrylic acid.

In the method for recovering (meth)acrylic acid, the above described respective processes may be performed systemically and continuously. In addition to the above described processes, the method may further include processes which are generally performed, before or after the respective processes, or at the same time.

According to another embodiment of the present invention, provided is an apparatus for recovering (meth)acrylic acid, including a distillation tower equipped with a feed inlet, and top, side, and bottom outlets; and a crystallizer equipped with a crude (meth)acrylic acid inlet connected to the side outlet of the distillation tower via a crude (meth) acrylic acid transfer line, and a (meth)acrylic acid outlet discharging (meth)acrylic acid obtained by recrystallization of the introduced crude (meth)acrylic acid.

The distillation tower 300 may be a packed column packed with a filler or a multistage tray column, and specifically, a sieve tray column or a dual flow tray column.

Further, the crystallizer 500 may be equipped with a tube and a circulating pump. In detail, the tube may be equipped with a reservoir capable of storing components to be recrystallized at the lower portion thereof. Further, the outer wall of the tube may include a double jacket to control an inner temperature of the tube. Such tube may have a length of about 0.5 to 2 m. Further, the components in the reservoir was transferred to the upper portion of the tube by the circulating pump and then allowed to flow as a falling film on the inner wall of the tube, thereby inducing deposition of crystals on the inner wall of the tube. However, the crystallizer may be any crystallizer which is generally used in the art to which the present invention pertains.

The recovering apparatus may further include a (meth) acrylic acid absorption tower equipped with a gas mixture inlet to which a (meth)acrylic acid-containing gas mixture is supplied, and an aqueous solution outlet discharging a (meth)acrylic acid solution obtained by contacting the gas mixture with the absorption solvent. The aqueous solution outlet of the absorption tower may be connected to the feed inlet of the distillation tower via the aqueous solution transfer line.

As the (meth)acrylic acid absorption tower, a packed tower or a multistage tray tower may be used in order to improve contact efficiency of the (meth)acrylic acid-containing gas mixture and the absorption solvent. Herein, the packed tower to which a filler such as raschig ring, pall ring, saddle, gauze, structured packing is applied may be used.

The recovering apparatus may further include a (meth) acrylic acid extraction tower equipped with an aqueous solution inlet connected to the aqueous solution outlet of the absorption tower via an aqueous solution transfer line, an extract outlet discharging the (meth)acrylic acid extract solution obtained by contacting the introduced (meth)acrylic acid solution with an extraction solvent, and a raffinate outlet discharging a raffinate solution after being left therein.

For example, the extract outlet of the extraction tower may be connected to the feed inlet of the distillation tower via the extract transfer line. Therefore, all the (meth)acrylic acid solution discharged from the absorption tower may be passed through the extraction tower and introduced into the distillation tower. For another example, the aqueous solution outlet of the absorption tower and the extract outlet of the extraction tower may be connected to the feed inlet of the distillation tower via the same or different transfer line. Therefore, a part of the (meth)acrylic acid solution discharged from the absorption tower may be supplied to the extraction tower, and the rest of the (meth)acrylic acid solution may be supplied to the distillation tower.

As the (meth)acrylic acid extraction tower, a general liquid-liquid contact extraction tower may be used without particular limitation. Non-limiting examples of the extraction tower may include a Karr type reciprocating plate column, a rotary-disk contactor, a Scheibel column, a Kuhni column, a spray extraction column, a packed extraction tower, a pulsed packed column.

In addition, the (meth)acrylic acid aqueous solution transfer line, the extract transfer line, the phase separator 350, and the high-boiling point by-product separation tower 400 may be constituted with those generally used in the art to which the present invention pertains. Further, the recovering apparatus may further include a constitution generally employed in the art to which the present invention pertains.

Hereinafter, actions and effects of the present invention will be described in more detail with reference to specific Examples. However, these are for illustrative purposes only, and the invention is not intended to be limited thereby.

Experimental Example 1: Comparison of Crude Acrylic Acids Obtained from Side and Bottom Portions of Distillation Tower Comparative Example 1

As a distillation tower 300 in a recovering apparatus of FIG. 1, a dual flow tray column having an inner diameter of 70 mm and total 30 sections was used, and an overhead pressure was controlled to 110 torr.

An acrylic acid solution containing 65.4% by weight of acrylic acid, 2.0% by weight of acetic acid, 31.8% by weight of water, and 0.8% by weight of other components was applied at a flow rate of about 35 g/min to a $14^{th}$ section placed fourteenth from the top portion of the distillation tower 300. A part of toluene reflux stream separated in a phase separator 350 was introduced as an azeotropic solvent into a first section, which is the uppermost section of the distillation tower. The amount of the toluene reflux stream to be introduced was controlled to a reflux ratio of about 5.5 (a flow ratio of a reflux solution to an effluent solution). In addition, the temperature of $16^{th}$ section was increased above 80° C. and the temperature of $12^{th}$ section was controlled below 65° C. by supplying heat to a reboiler at the bottom of the distillation tower 300. After operation was stably performed for 10 hours, a distillation product was obtained at a flow rate of about 85 g/min from the top portion of the distillation tower 300, and an acrylic acid stream (Stream 1 of FIG. 1) from which most water was removed was obtained at a flow rate of about 22 g/min from the bottom portion of the distillation tower 300 in a steady state.

Example 1

As a distillation tower 300 in a recovering apparatus of FIG. 2, a dual flow tray column having an inner diameter of 70 mm and total 30 sections was used, and an overhead pressure was controlled to 110 torr.

An acrylic acid solution containing 65.4% by weight of acrylic acid, 2.0% by weight of acetic acid, 31.8% by weight of water, and 0.8% by weight of other components was applied at a flow rate of about 35 g/min to a $14^{th}$ section placed fourteenth from the top portion of the distillation tower 300. A part of toluene reflux stream separated in a phase separator 350 was introduced as an azeotropic solvent into a first section, which is the uppermost section of the distillation tower. The amount of the toluene reflux stream to be introduced was controlled to a reflux ratio of about 5.7 (a flow ratio of a reflux solution to an effluent solution). In addition, the temperature of $16^{th}$ section was increased above 85° C. and the temperature of $12^{th}$ section was controlled below about 65° C. by supplying heat to a reboiler at the bottom of the distillation tower 300. After operation was stably performed for 10 hours, a distillation product was obtained at a flow rate of about 85 g/min from the top portion of the distillation tower 300, and a stream (Stream 1 of FIG. 2) containing high-boiling point by-products was obtained at a flow rate of about 11.5 g/min from the bottom portion of the distillation tower 300 in a steady state. Further, a liquid-phase crude acrylic acid stream (Stream 2 of FIG. 2) was obtained at a flow rate of about 11 g/min from a 30$^{th}$ section placed thirtieth from the top portion of the distillation tower 300, and the content of the acrylic acid in the crude acrylic acid obtained in the 30$^{th}$ section was about 49% by weight of the total acrylic acid.

Example 2

A distillation product was obtained at a flow rate of about 85 g/min from the top portion of the distillation tower 300, a stream (Stream 1 of FIG. 2) containing high-boiling point by-products was obtained at a flow rate of about 4 g/min from the bottom portion of the distillation tower 300, and a liquid-phase crude acrylic acid stream (Stream 2 of FIG. 2) was obtained at a flow rate of about 18.5 g/min from the 30$^{th}$ section of the distillation tower 300 by performing operation in the same manner as in Example 1, except that a flow rate of the side flow discharge pump was controlled so that the amount of acrylic acid obtained in the 30$^{th}$ section was about 84% by weight of the total acrylic acid.

Example 3

As a distillation tower 300 in a recovering apparatus of FIG. 2, a dual flow tray column having an inner diameter of 70 mm and total 30 sections was used, and a side discharge tube was placed in the gas phase distinguished from the liquid phase on a tray in order to obtain gas-phase crude acrylic acid from a 30$^{th}$ section placed thirtieth from the top portion of the distillation tower 300. As the side discharge tube, a side discharge tube equipped with a condenser was used in order to discharge condensed gas-phase crude acrylic acid. The side discharge tube was inserted as above, and the overhead pressure of the distillation tower was controlled to 110 torr.

An acrylic acid solution containing 65.4% by weight of acrylic acid, 2.0% by weight of acetic acid, 31.8% by weight of water, and 0.8% by weight of other components was applied at a flow rate of about 35 g/min to a 14$^{th}$ section placed fourteenth from the top portion of the distillation tower 300. A part of toluene reflux stream separated in a phase separator 350 was introduced as an azeotropic solvent into a first section, which is the uppermost section of the distillation tower. The amount of the toluene reflux stream to be introduced was controlled to a reflux ratio of about 5.7 (a flow ratio of a reflux solution to an effluent solution). In addition, the temperature of 16$^{th}$ section was increased above 80° C. and the temperature of 12$^{th}$ section was controlled below 70° C. by supplying heat to a reboiler at the bottom of the distillation tower 300. After operation was stably performed for 10 hours, a distillation product was obtained at a flow rate of about 85 g/min from the top portion of the distillation tower 300, and a stream (Stream 1 of FIG. 2) containing high-boiling point by-products was obtained at a flow rate of about 10 g/min from the bottom portion of the distillation tower 300 in a steady state. Further, a gas-phase crude acrylic acid stream (Stream 2 of FIG. 2) was obtained at a flow rate of about 12 g/min from a 30$^{th}$ section placed thirtieth from the top portion of the distillation tower 300, and the amount of the acrylic acid obtained in the 30$^{th}$ section was about 55% by weight of the total acrylic acid.

Example 4

A distillation product was obtained at a flow rate of about 85 g/min from the top portion of the distillation tower 300, a stream (Stream 1 of FIG. 2) containing high-boiling point by-products was obtained at a flow rate of about 5 g/min from the bottom portion of the distillation tower 300, and a gas-phase crude acrylic acid stream (Stream 2 of FIG. 2) was obtained at a flow rate of about 18 g/min from the 30$^{th}$ section of the distillation tower 300 by performing operation in the same manner as in Example 3, except that a discharge pressure of the condenser equipped in the side discharge tube is reduced so that the amount of acrylic acid obtained in the 30$^{th}$ section was about 79% by weight of the total acrylic acid.

To compare the acrylic acid mixture, from which most water was removed, obtained in Comparative Example 1 with the crude acrylic acids obtained in Examples 1 to 4, the composition, recovery rate, and color thereof are given in Table 1.

TABLE 1

|  | Comparative Example 1 | Example 1 | Example 2 | Example 3 | Example 4 |
|---|---|---|---|---|---|
| Amount discharged from side portion[1] | — | 49% by weight | 84% by weight | 55% by weight | 79% by weight |
| Phase discharged from side portion[2] | — | liquid phase | liquid phase | gas phase | gas phase |
| Reboiler temperature | 137.5° C. | 137.8° C. | 139.5° C. | 139.9° C. | 142.4° C. |
| Acrylic acid recovery rate | 98.6% | 99.0% | 98.6% | 99.1% | 99.0% |

|  | Component in tower bottom | Component in tower side | Component in tower bottom | Component in tower side | Component in tower bottom | Component in tower side | Component in tower bottom | Component in tower side | Component in tower bottom |
|---|---|---|---|---|---|---|---|---|---|
| Toluene | 0 | 0 | 0 | 0 | 0 | 0.005 | 0 | 0.004 | 0 |
| Acetic acid | 0.066 | 0.135 | 0.069 | 0.086 | 0.044 | 0.137 | 0.082 | 0.129 | 0.067 |
| Furfural | 0.019 | 0.018 | 0.028 | 0.018 | 0.031 | 0.013 | 0.026 | 0.021 | 0.032 |
| Benzaldehyde | 0.026 | 0.016 | 0.038 | 0.016 | 0.046 | 0.009 | 0.036 | 0.019 | 0.047 |
| DAA[3] | 5.3 | 0.060 | 5.2 | 0.079 | 10.0 | 0.011 | 6.0 | 0.013 | 9.2 |
| Hydroquinone | 0.193 | 0.027 | 0.346 | 0.027 | 0.536 | 0 | 0.340 | 0 | 0.478 |
| Propionic acid | 0.026 | 0.027 | 0.026 | 0.027 | 0.023 | 0.027 | 0.026 | 0.027 | 0.025 |
| Water | 0.024 | 0.012 | 0.035 | 0.019 | 0.039 | 0.017 | 0.028 | 0.024 | 0.046 |

TABLE 1-continued

| Acrylic acid | 92.8 | 99.3 | 91.8 | 99.8 | 83.9 | 99.8 | 92.0 | 99.8 | 87.6 |
|---|---|---|---|---|---|---|---|---|---|
| APHA[4] | >500 | 360 | | 368 | | 3 | | 3 | |

(Unit of crude acrylic acid: % by weight)
[1] Amount discharged from side portion: a weight ratio of acrylic acid discharged from the side portion of the distillation tower to the total acrylic acid contained in the acrylic acid solution supplied to the distillation tower
[2] Phase discharged from side portion: phase of crude acrylic acid obtained from the side portion of the distillation tower
[3] DAA: acrylic acid dimer
[4] APHA: a color index measured in accordance with APHA, ASTM D1209, in which the lower value means that it is closer to colorless and the higher value means that it is closer to yellow.

Referring to Table 1, crude acrylic acids obtained from the side portion in Examples 1 to 4 were found to include a smaller amount of high-boiling point acrylic acid dimer than that of Comparative Example 1, and their colors according to APHA were found to be closer to colorless. Further, crude acrylic acids obtained in Examples 3 and 4 were found to include a smaller amount of high-boiling point acrylic acid dimer than those of Examples 1 and 2, and crude acrylic acids having the color value of about APHA 3 were obtained through a water distillation tower.

Experimental Example 2: Comparison of Recrystallization Results Between Crude Acrylic Acids Obtained from Side and Bottom Portions of Distillation Tower Comparative Example 2

For recrystallization of the acrylic acid stream (stream 1 of FIG. 1), from which most water was removed, obtained from the bottom portion of distillation tower 300 of Comparative Example 1, a crystallizer 500 equipped with a glass tube and a circulating pump was prepared. The glass tube was equipped with a reservoir at the bottom portion thereof, and its length was 1 m and ID was 1 inch, and the outer wall thereof included a double jacket to control an inner temperature of the tube at a constant level. As the circulating pump, a circulating pump which transfers the liquid in the reservoir to the upper portion of the glass tube and allows the liquid to flow in the form of a falling film in the inner wall of the glass tube was prepared.

The acrylic acid mixture (stream 1 of FIG. 1) obtained from the bottom portion of the distillation tower 300 of Comparative Example 1 was directly introduced into the reservoir of the prepared crystallizer 500. The acrylic acid mixture introduced into the reservoir was allowed to flow in the form of a falling film in the inner wall of the glass tube by the circulating pump, and a temperature of the double jacket of the glass tube was decreased below a freezing point of acrylic acid. As a result, about 70 to 85% by weight of acrylic acid was crystallized in the inner wall of the glass tube. Thereafter, the circulating pump was stopped, and the temperature of the jacket was increased near the freezing point of acrylic acid to sweat about 5% by weight of acrylic acid. After sweating, the residual solution was discharged by a pump. Subsequently, the temperature of the double jacket of the glass tube was increased above the freezing point of acrylic acid to melt the crystals formed in the inner wall of the glass tube, which was discharged by the pump. The melted acrylic acid was used as a feed in a subsequent crystallization step to repeat the above dynamic crystallization twice. Consequently, recrystallized acrylic acid was obtained through the total three cycles of the dynamic crystallization process.

Comparative Example 3

The acrylic acid stream (stream 1 of FIG. 1) obtained from the bottom portion of the distillation tower 300 of Comparative Example 1 was introduced at a flow rate of 22 g/min into a high-boiling point by-product separation tower 400 of the recovering apparatus of FIG. 1. The overhead temperature was controlled above about 60° C. by a reboiler at the bottom portion of the high-boiling point by-product separation tower 400. After operation was stably performed for 10 hours, a crude acrylic acid stream (Stream 2 of FIG. 1) was obtained at a flow rate of about 20 g/min from the top portion of the high-boiling point by-product separation tower 400 in a steady state. The crude acrylic acid stream (Stream 2 of FIG. 1) included 0.16% by weight of acetic acid, 0.02% by weight of furfural, 0.003% by weight of benzaldehyde, 0.0097% by weight of acrylic acid dimer, 0.029% by weight of propionic acid, 0.08% by weight of water, and 99.6% by weight of acrylic acid.

The crude acrylic acid stream (Stream 2 of FIG. 1) was supplied to the crystallizer 500, and recrystallization was performed under the same conditions as in Comparative Example 2 to obtain recrystallized acrylic acid (Stream 3 of FIG. 1).

Example 5

The liquid-phase crude acrylic acid stream (Stream 2 of FIG. 2) obtained from the side portion of the distillation tower 300 of Example 2 was directly supplied to the crystallizer 500. Subsequently, recrystallization was performed under the same conditions as in Comparative Example 2 to obtain recrystallized acrylic acid (Stream 3 of FIG. 2).

Example 6

The gas-phase crude acrylic acid stream (Stream 2 of FIG. 2) obtained from the side portion of the distillation tower 300 of Example 4 was directly supplied to the crystallizer 500. Subsequently, recrystallization was performed under the same conditions as in Comparative Example 2 to obtain recrystallized acrylic acid (Stream 3 of FIG. 2).

The composition of impurities included in the recrystallized acrylic acids obtained in Comparative Examples 2 to 3 and Examples 5 to 6 and the color of the recrystallized acrylic acids according to APHA are given in Table 2.

TABLE 2

| | Comparative Example 2 | Comparative Example 3 | Example 5 | Example 6 |
|---|---|---|---|---|
| Toluene | 0 | 0 | 0 | 0 |
| Acetic acid | 198 | 320 | 208 | 282 |
| Furfural | 9 | 0 | 2 | 0 |
| Benzaldehyde | 9 | 0 | 0 | 0 |
| DAA | 761 | 11 | 157 | 47 |

TABLE 2-continued

|  | Comparative Example 2 | Comparative Example 3 | Example 5 | Example 6 |
|---|---|---|---|---|
| Hydroquinone | 110 | 0 | 0 | 0 |
| Propionic acid | 128 | 101 | 106 | 103 |
| Water | 275 | 126 | 387 | 109 |
| Maleic acid | 310 | 2 | 24 | 6 |
| APHA | 135 | 3 | 7 | 3 |

(Unit of impurity content: ppm)

Referring to Table 2, even though the acrylic acid stream obtained from the bottom portion of the water distillation tower 300 as in Comparative Example 2 underwent the crystallization process, the product had the color of APHA 135, and thus it could not be used as a high-purity product. In contrast, the crude acrylic acid streams obtained from the side portion of the water distillation tower 300 as in Examples 5 and 6 had the colors of APHA 7 and 3, respectively after the crystallization process, and thus they are suitable to be used as high-purity products. In particular, even though Examples 5 and 6 were not passed through the high-boiling point by-product separation tower, they were found to provide acrylic acid having purity as high as that of Comparative Example 3 passed through the high-boiling point by-product separation tower. Therefore, it was confirmed that the method for recovering acrylic acid according to Examples is used to efficiently recover high-purity acrylic acid.

The invention claimed is:

1. A method for recovering (meth)acrylic acid, comprising a distillation process of distilling a feed including 10 to 90% by weight of (meth)acrylic acid, 10 to 90% by weight of a solvent, and a residual amount of impurity to obtain crude (meth)acrylic acid including 80% by weight or more of (meth)acrylic acid, 5% by weight or less of the solvent, and 3% by weight or less of (meth)acrylic acid dimer from the side portion of a distillation tower and a high-boiling point by-product separation process of obtaining crude (meth)acrylic acid from a top portion of a high-boiling point by-product separation tower by distilling a bottom discharge liquid obtained from a bottom portion of the distillation tower.

2. The method of claim 1, further comprising an absorption process of obtaining a (meth)acrylic acid solution by contacting a (meth)acrylic acid-containing gas mixture with an absorption solvent.

3. The method of claim 2, further comprising an extraction process of obtaining a (meth)acrylic acid extract solution and a raffinate solution by contacting the (meth)acrylic acid solution with an extraction solvent.

4. The method of claim 1, wherein the crude (meth)acrylic acid is discharged from a section placed 50% to 100% from the top section of the distillation tower.

5. The method of claim 1, wherein a liquid-phase or gas-phase crude (meth)acrylic acid is obtained from the side portion of the distillation tower.

6. The method of claim 1, wherein (meth)acrylic acid corresponding to 30 to 90% by weight of the total (meth)acrylic acid contained in the feed is recovered from the side portion of the distillation tower.

7. The method of claim 1, further comprising a crystallization process of recrystallizing the crude (meth)acrylic acid.

* * * * *